US012089950B2

(12) United States Patent
Findlay et al.

(10) Patent No.: US 12,089,950 B2
(45) Date of Patent: Sep. 17, 2024

(54) WEARABLE DEVICE

(71) Applicant: Buddi Limited, Rickmansworth (GB)

(72) Inventors: Ewan Findlay, Rickmansworth (GB);
Niall Laing, Rickmansworth (GB);
Sara Murray, Rickmansworth (GB);
Edward Barnard, Rickmansworth (GB)

(73) Assignee: Buddi Limited, Rickmansworth (GB)

( * ) Notice: Subject to any disclaimer, the term of this patent is extended or adjusted under 35 U.S.C. 154(b) by 0 days.

(21) Appl. No.: 18/542,552

(22) Filed: Dec. 15, 2023

(65) Prior Publication Data
US 2024/0115198 A1    Apr. 11, 2024

Related U.S. Application Data

(63) Continuation of application No. PCT/GB2022/051487, filed on Jun. 14, 2022.

(30) Foreign Application Priority Data

Jun. 30, 2021 (GB) ..................................... 2109491

(51) Int. Cl.
*A61B 5/00* (2006.01)
(52) U.S. Cl.
CPC .......... *A61B 5/4845* (2013.01); *A61B 5/0022* (2013.01); *A61B 5/681* (2013.01); *A61B 2560/0247* (2013.01)
(58) Field of Classification Search
CPC ..... A61B 5/4845; A61B 5/0022; A61B 5/681; A61B 2560/0247; A61B 5/1112;
(Continued)

(56) References Cited

U.S. PATENT DOCUMENTS 5,220,919 A    6/1993   Phillips et al.
7,311,665 B2  12/2007   Hawthorne et al.
(Continued)

FOREIGN PATENT DOCUMENTS

GB    2484017 B     7/2015
JP    2010107414 A  5/2010
(Continued)

OTHER PUBLICATIONS

GB Patent Application No. GB2109491.7; UKIPO Search Report dated Dec. 23, 2021; 7 pages.
(Continued)

*Primary Examiner* — Freddie Kirkland, III
(74) *Attorney, Agent, or Firm* — Haynes and Boone, LLP

(57) ABSTRACT

There is presented a wearable device (200) and corresponding system and method for sensing a substance ingested by a subject, for instance an intoxicating substance. The wearable device has a sensing arrangement extending between a first port (205*a*) and a second port (205*b*). The sensing arrangement includes two chambers, a pump and two flow-control devices. The first chamber is adapted to collect gas from a skin region of the subject. The second chamber has a sensor to sense the substance. The first flow-control device is provided at the first port (205*a*) and the second flow-control device is provided at the second port (205*b*). A controller is provided to control the pump and the sensor. The controller is operable in a first phase to sense a first gas sample from ambient environment, and a second phase to sense a second gas sample from a skin region of the subject.

22 Claims, 10 Drawing Sheets

Figure 1:
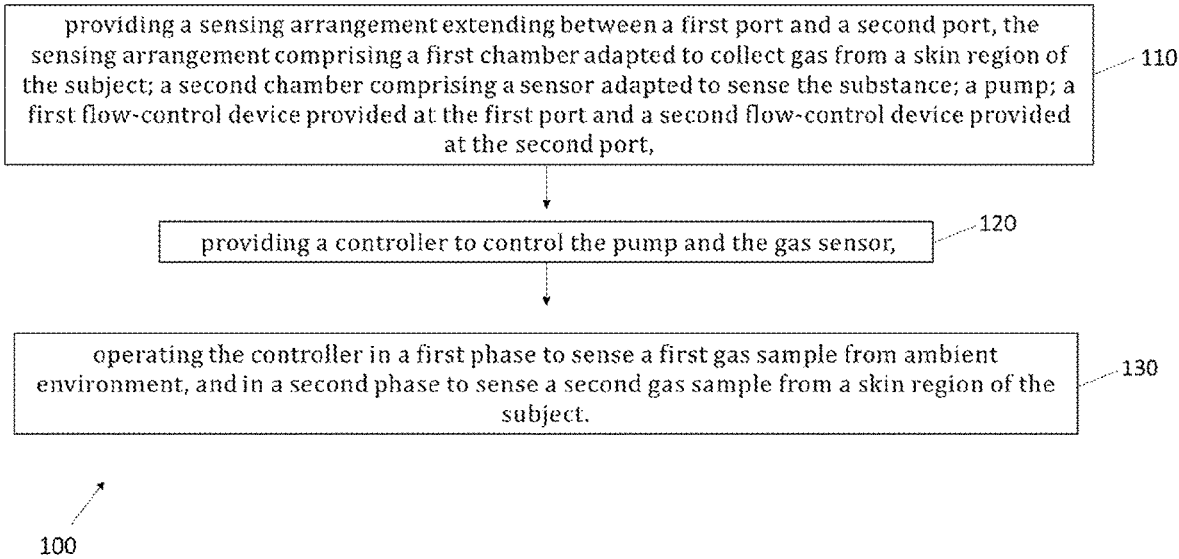

(58) Field of Classification Search
CPC .......... A61B 5/443; A61B 5/7203; A61B 2560/0252; A61B 2562/029; A61B 5/4266; G01N 33/0016; G01N 33/4972
See application file for complete search history.

(56) References Cited

U.S. PATENT DOCUMENTS

| | | | |
|---|---|---|---|
| 7,462,149 | B2 | 12/2008 | Hawthorne et al. |
| 7,611,461 | B2 | 11/2009 | Hawthorne et al. |
| 7,641,611 | B2 | 1/2010 | Hawthorne et al. |
| 7,930,927 | B2 | 4/2011 | Cooper et al. |
| 8,165,824 | B2 | 4/2012 | Iiams et al. |
| 8,317,697 | B2 | 11/2012 | Hawthorne et al. |
| 8,379,313 | B2 * | 2/2013 | Shimomura ............. B41J 2/473 347/256 |
| 9,480,431 | B2 | 11/2016 | Melton |
| 9,829,480 | B2 * | 11/2017 | Wojcik ................ G06V 40/167 |
| 11,278,222 | B2 * | 3/2022 | Moeller ............... G01N 27/403 |
| 2009/0182216 | A1 | 7/2009 | Roushey, III et al. |
| 2011/0015873 | A1 | 1/2011 | Iiams et al. |
| 2013/0006066 | A1 | 1/2013 | Melton |
| 2015/0212063 | A1 | 7/2015 | Wojcik et al. |
| 2016/0262657 | A1 | 9/2016 | Ahmad et al. |

FOREIGN PATENT DOCUMENTS

| | | |
|---|---|---|
| JP | 2012193992 A | 10/2012 |
| WO | WO 2011/008731 A1 | 1/2011 |
| WO | WO 2015/143384 A1 | 9/2015 |

OTHER PUBLICATIONS

PCT/GB2022/051487 International Preliminary Report on Patentability, dated Jun. 15, 2023; 20 pages.
PCT/GB2022/051487 International Search Report and Written Opinion, mailed Sep. 30, 2022; 16 pages.
Third Party Observations under Section 21, Apr. 11, 2023; 5 pages.
ALCOTEST 9500 Technical Manuat, Washington Technical Manual V3.2, 2016; 33 pages.
Home Office Centre for Applied Science and Technology, "Report on the Evaluation of Purge/Blank Cycle on the Intoximeter EC/IR", Report No. BA 02/16; v1.0 Jun. 2016.

* cited by examiner

WEARABLE DEVICE

CROSS REFERENCE TO RELATED APPLICATIONS

This application is a continuation of International Application No. PCT/GB2022/051487, filed Jun. 14, 2022, which claims priority to Great Britain Pat. Application No. 210949.1, filed Jun. 30, 2021, the contents of both of which are hereby incorporated by reference in its entirety as though fully set forth herein.

TECHNICAL FIELD

The present disclosure relates to a wearable device for sensing a substance ingested by a subject, such as alcohol.

BACKGROUND

Transdermal alcohol detection can be used as a means of monitoring the alcohol intake of a subject, usually under a judicial court order. A device is held in close proximity to the subject's skin, usually by an ankle strap, and can broadcast to a remote computer system the air-alcohol-concentration measured from air drawn directly from the direction of the wearer's skin. An example of such a device is the alcohol monitoring SCRAM device which is designed to report the subject's location as derived from GPS or an RF beacon as well as its intake of intoxicating substances (U.S. Pat. No. 7,641,611).

Various other systems have been reported for monitoring an intoxicating substance. For instance, U.S. Pat. Nos. 5,220,919A and 7,930,927B2 describe trans-dermal fuel-cell based alcohol monitors. Document US20150212063 describes an image user-verification breathalyser. Document US20130006066 describes a system provided with multiple sensors distributed around the exterior of the device.

Wearable intoxication monitors which operate by monitoring air proximal to the subject's skin suffer from of airborne interferants that give signals similar to that of the target intoxicant. For instance, a device may be monitoring for ethanol consumption by looking for traces of ethanol in sweat by drawing air from next to the subject's ankle, but instead detects atmospheric alcohols, which may or may not be ethanol, and reports the resulting signals as an ethanol intoxication event.

Algorithmic means of differentiating such events on the basis of the time it takes for ethanol to pass through the subject's system have been suggested in U.S. Pat. No. 8,165,824. However, such algorithms result in a delay in the detection of an intoxication event and restrict the usefulness of the device. For instance, if a subject has been told to wear the device as part of a drug monitoring scheme aimed at reducing violent behaviour whilst intoxicated, its output is only available as proof of drug taking prior to a violent act and not, as one might hope, a means of preventing that violent act in the first place.

It is an object of the disclosure to address one or more of the above-mentioned limitations.

SUMMARY

According to a first aspect of the disclosure there is provided a wearable device for sensing a substance ingested by a subject, the wearable device comprising a sensing arrangement extending between a first port and a second port, the sensing arrangement comprising a first chamber adapted to collect gas from a skin region of the subject; a second chamber comprising a sensor adapted to sense the substance; a pump; a first flow-control device provided at the first port; a second flow-control device provided at the second port; and a controller adapted to control the pump and the sensor, the controller being operable in a first phase to sense a first gas sample from ambient environment, and a second phase to sense a second gas sample from a skin region of the subject; wherein in the first phase the controller is configured to enable the pump for a first duration to open the first flow-control device and the second flow-control device and provide the second chamber with a first gas sample from ambient environment; wherein in the second phase the controller is configured to enable the pump for a second duration to provide the second chamber with a second gas sample from the first chamber.

Optionally, each one of the first flow-control device and the second flow-control device is operable between a first state and a second state based on a pressure difference between an inner side and an outer side of the flow-control device, wherein in the first state the flow-control device pass a gas flow and wherein in the second state the flow-control device stops the gas flow.

Optionally, wherein in the first phase the controller is configured to disable the pump to close the first flow-control device and the second flow-control device; to enable the sensor to sense the first gas sample to obtain a first quantity of the substance; wherein in the second phase the controller is configured to disable the pump; to enable the sensor to sense the second gas sample to obtain a second quantity of the substance.

Optionally the first duration is greater than the second duration, or the first duration is substantially equal to the second duration. For instance, the first duration may be long enough to reduce an internal pressure below a pre-determined value so that the first flow-control device pass a gas flow. For instance, the second duration is such that the internal pressure remains above a certain value such that the first flow-control device stops the gas flow.

Optionally, the controller is configured to delay the start of the second phase by a delay-period.

Optionally, during the delay-period gas is diffusing from the skin portion into the first chamber.

Optionally, the controller is operable in a third phase, wherein in the third phase the controller is configured to enable the pump for a third duration to open the first flow-control device and the second flow-control device and provide the second chamber with another gas sample from ambient environment.

For instance the third duration may be greater than the first duration. For example the third duration may be sufficiently long to purge the second chamber.

Optionally, wherein in the third phase the controller is configured to disable the pump to close the first flow-control device and the second flow-control device; and to delay the start of the first phase by a predetermined delay-period.

Optionally, the pump is provided between the first chamber and the second chamber.

For example, the pump may be coupled to the first chamber via an isolation valve.

Optionally, the first chamber is provided between the pump and the second chamber.

Optionally, the first chamber comprises a flow profile adjuster.

Optionally, the flow profile adjuster is adapted to provide a laminar flow at the input of the first chamber.

Optionally, the flow profile adjuster comprises a mesh structure or a piston mechanism or a labyrinth structure.

Optionally, the first chamber comprises a membrane applicable on a skin portion of the subject.

For instance, the membrane may be a diffusion membrane, for example a waterproof diffusion membrane. For example, the membrane may be an expanded polytetrafluoroethylene (PTFE) membrane.

Optionally, the first chamber comprises a piston mechanism.

Optionally, the wearable device comprises one or more removable layers provided on the outer surface of the membrane.

Optionally, wherein the first flow-control device is a first-valve and wherein the second flow-control device is a second-valve.

For example, the first valve may be a one way valve adapted to pass a gas flow when a pressure difference between the outer side and the inner side of the first valve is above a first threshold value. The second valve may be a one way valve adapted to pass a gas flow when a pressure difference between the inner side and the outer side of the second valve is above a second threshold value.

Optionally, wherein the first flow-control device is a first-membrane and wherein the second flow-control device is a second-membrane.

For example, the first and second membranes may be waterproof membranes such as expanded polytetrafluoroethylene membranes. The first membrane may be adapted to allow diffusion through it when a first pressure difference is applied across the first membrane. Similarly, the second membrane may be adapted to allow diffusion through it when a second pressure difference is applied across the second membrane.

Optionally, the second chamber comprises at least one of a temperature sensor and a humidity sensor.

Optionally, the wearable device comprises a calculator adapted to calculate a difference between the first quantity and the second quantity and to return an output indicative of one of an ingestion and a lack of ingestion of the substance by the subject, based on the difference.

Optionally, the wearable device comprises a communication module adapted to send data from the sensing arrangement.

Optionally, at least one of the first port and the second port are provided with a terminator.

Optionally, the wearable device comprises a timer and a location device for acquiring time and a location data, wherein upon identification of the substance, the wearable device is configured to perform at least one of storing and transmitting the time and location data.

Optionally, the wearable device comprising a submersion detector adapted to detect when the device is put underwater.

According to a second aspect of the disclosure, there is provided a system for detecting ingestion by a subject of a substance of interest, the system comprising a wearable device according to the first aspect and a processor adapted to calculate a difference between a first quantity of the substance and a second quantity of the substance and to return an output indicative of one of an ingestion and a lack of ingestion of the substance by the subject, based on the difference.

The system according to the second aspect of the disclosure may comprise any of the features described above in relation to the wearable device according to the first aspect of the disclosure.

According to a third aspect of the disclosure, there is provided a method of sensing a substance ingested by a subject, the method comprising
providing a sensing arrangement extending between a first port and a second port, the sensing arrangement comprising a first chamber adapted to collect gas from a skin region of the subject; a second chamber comprising a sensor adapted to sense the substance; a pump; a first flow-control device provided at the first port and a second flow-control device provided at the second port,
providing a controller to control the pump and the sensor, and
operating the controller in a first phase to sense a first gas sample from ambient environment, and in a second phase to sense a second gas sample from a skin region of the subject;
wherein in the first phase the controller is configured to enable the pump for a first duration to open the first flow-control device and the second flow-control device and provide the second chamber with a first gas sample from ambient environment; wherein in the second phase the controller is configured to enable the pump for a second duration to provide the second chamber with a second gas sample from the first chamber.

Optionally the method comprises
obtaining a first quantity of the substance from the first gas sample and a second quantity of the substance from the second gas sample,
calculating a difference between the first quantity and the second quantity,
identifying one of an ingestion and a lack of ingestion of the substance by the based on the difference.

The options described with respect to the first aspect of the disclosure are also common to the third aspect of the disclosure.

DESCRIPTION

Figures 2A, 2B:
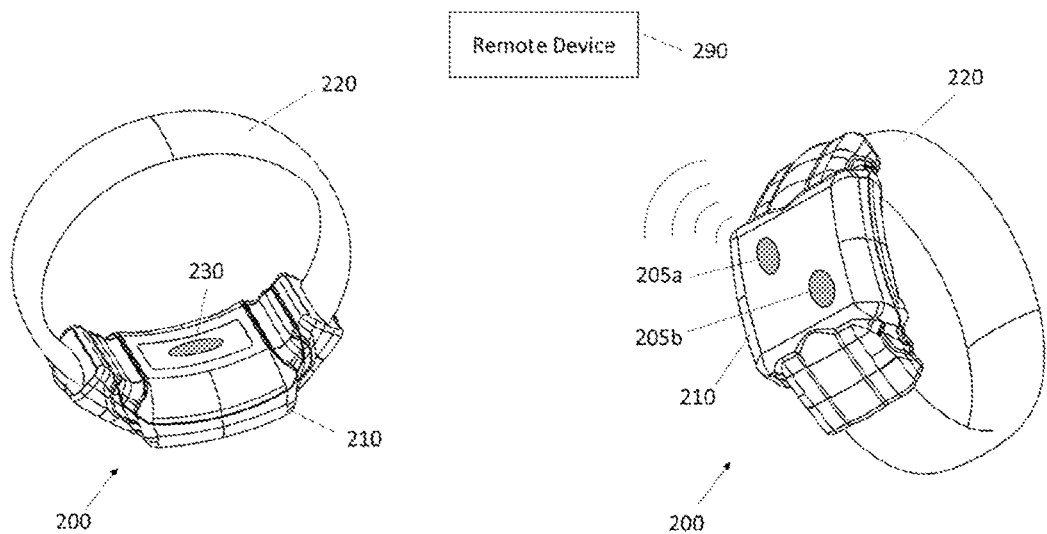
Figure 3:
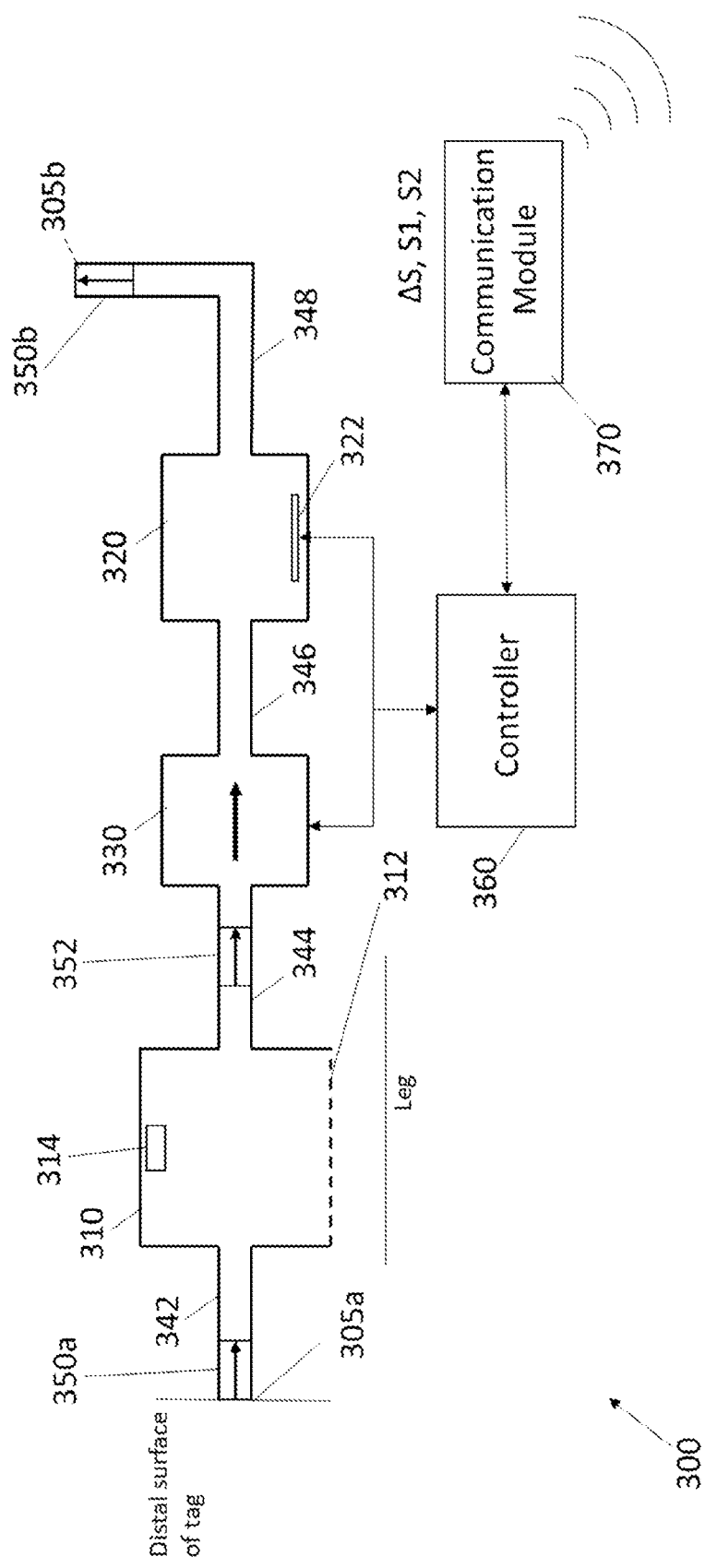
Figure 4:
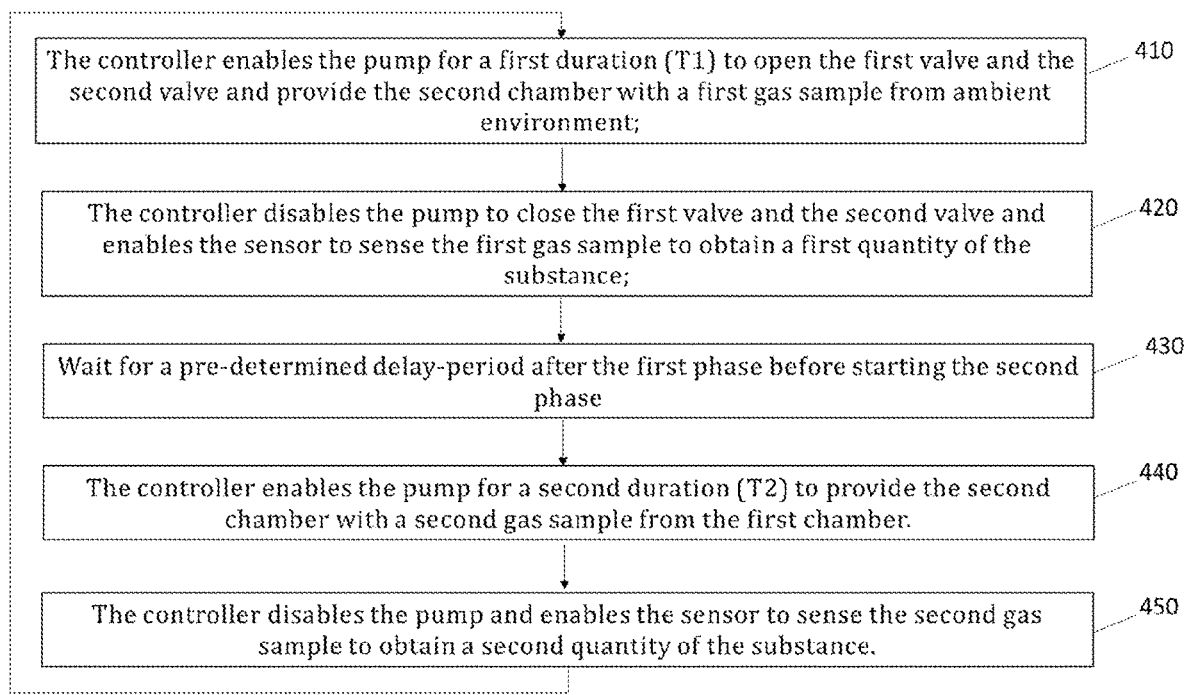
Figure 5:
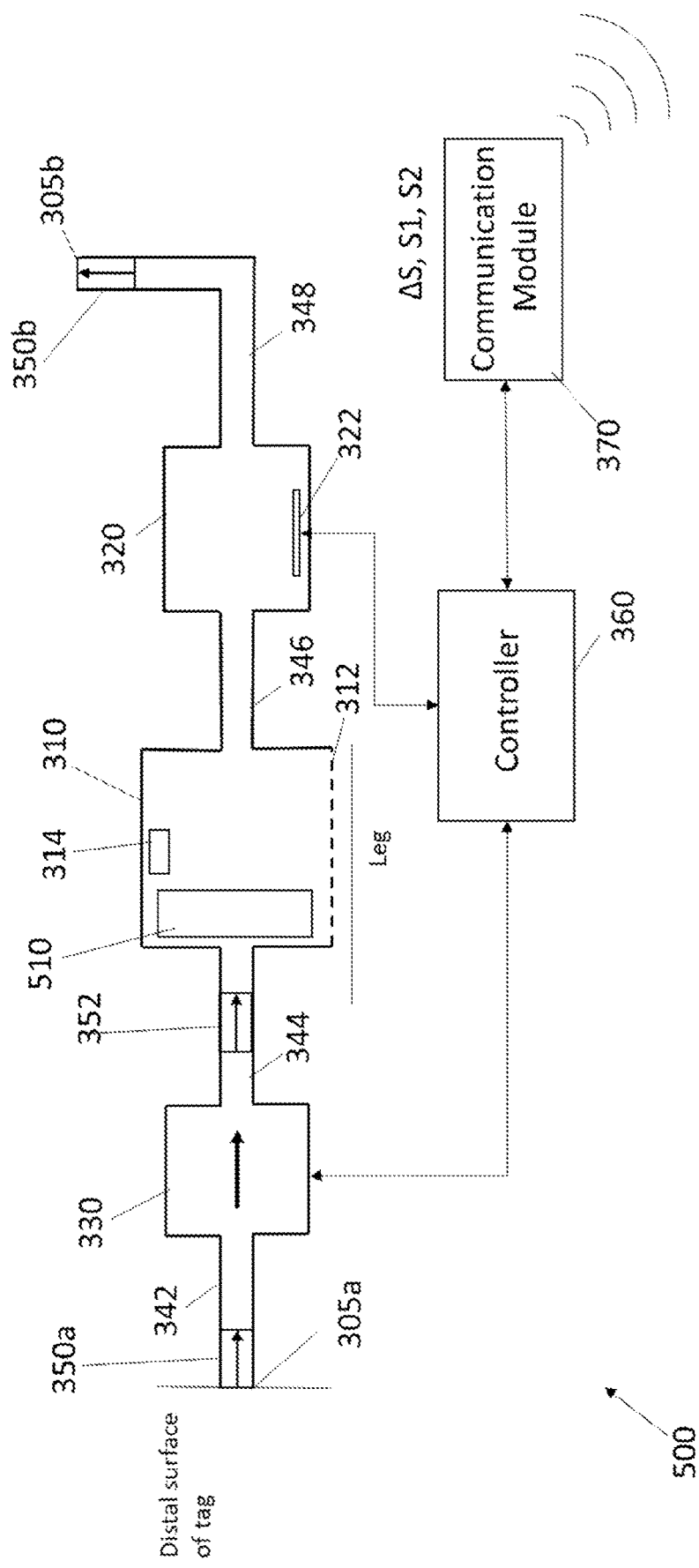
Figure 6:
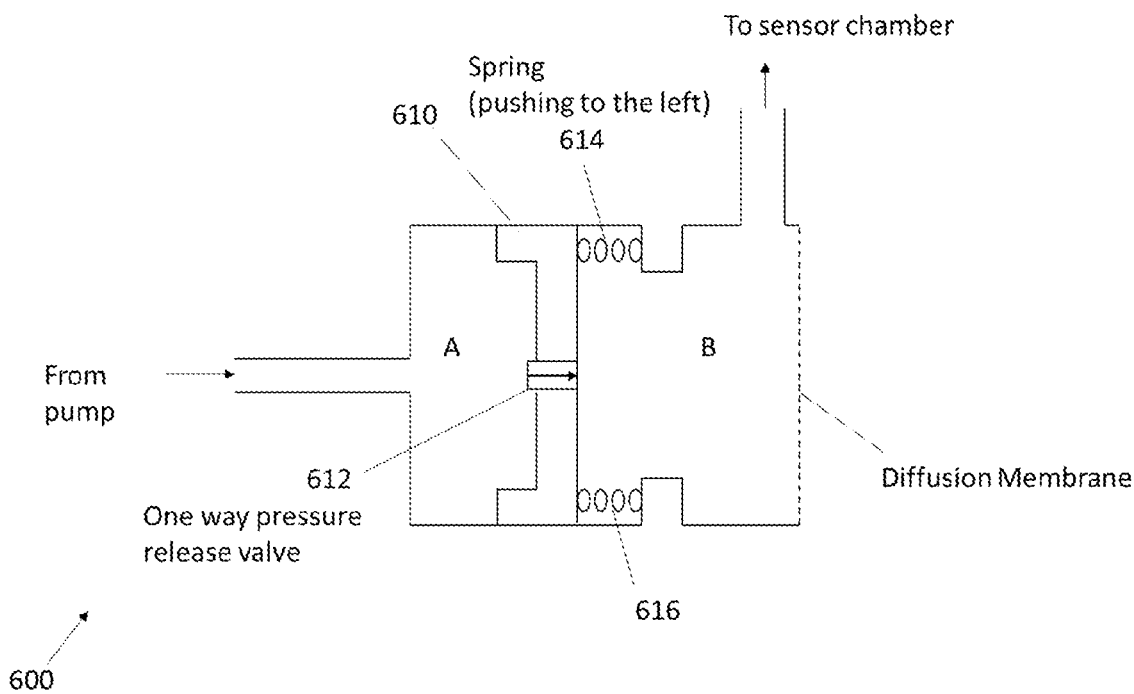
Figure 7:
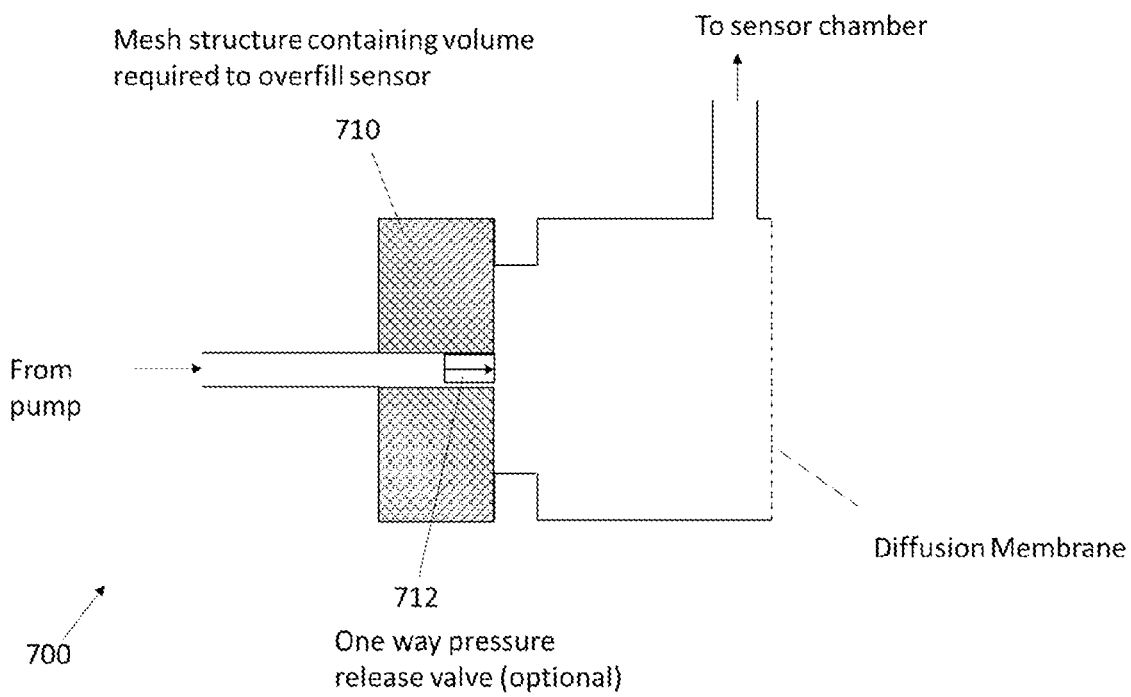
Figure 8:
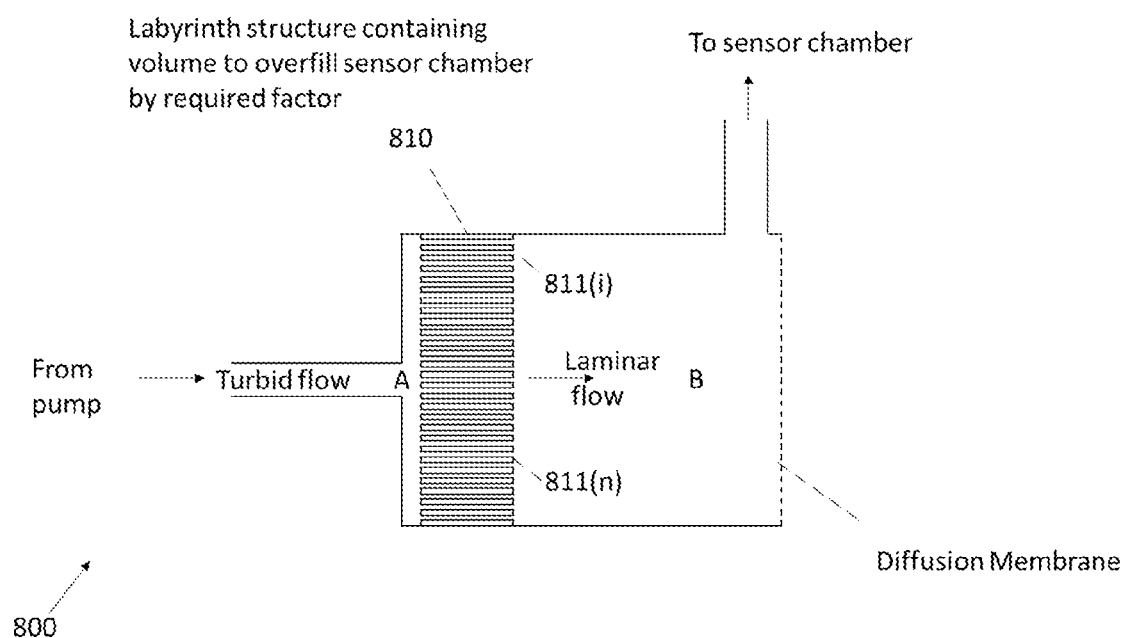
Figure 9A:
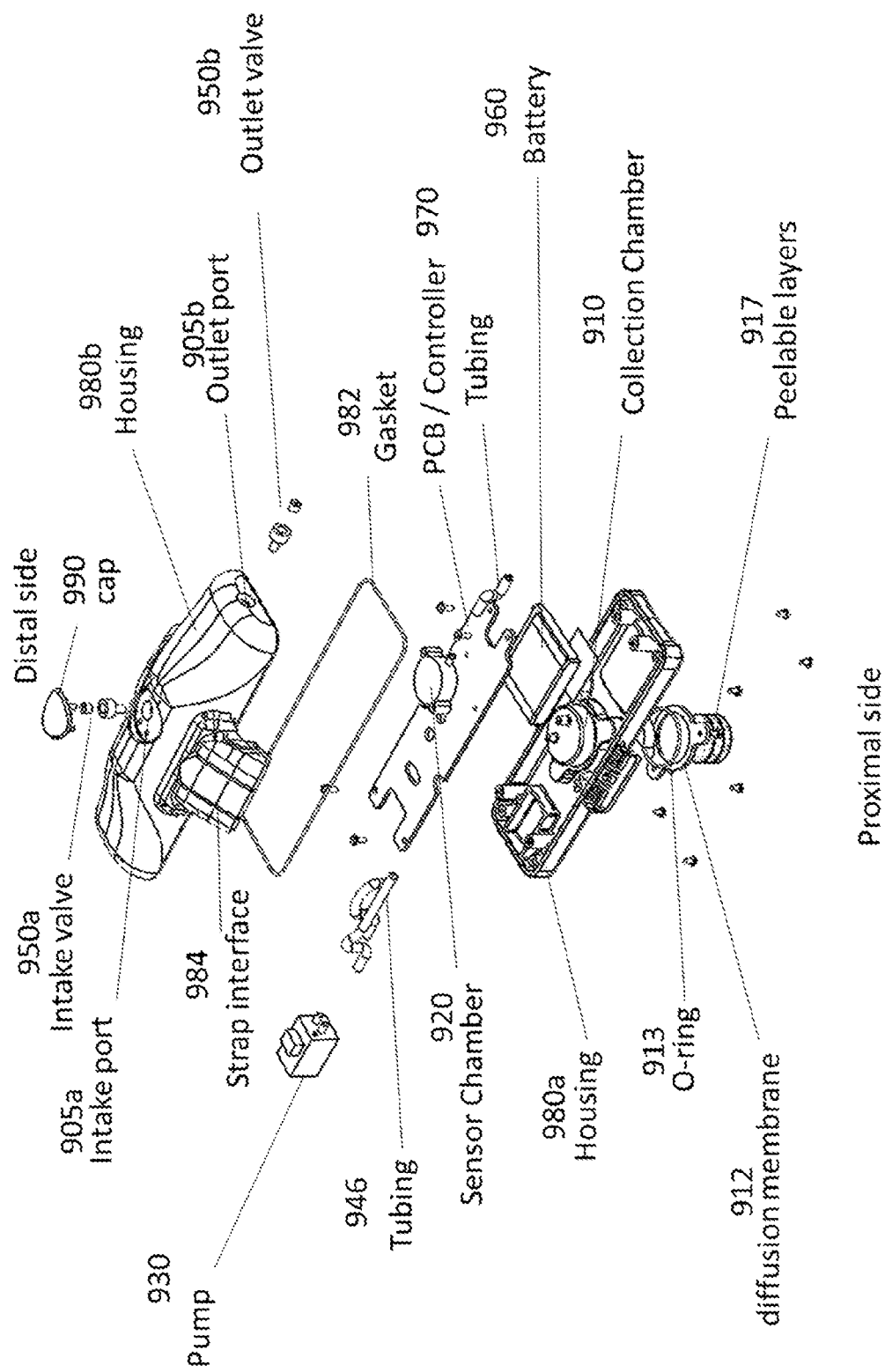
Figure 9B:
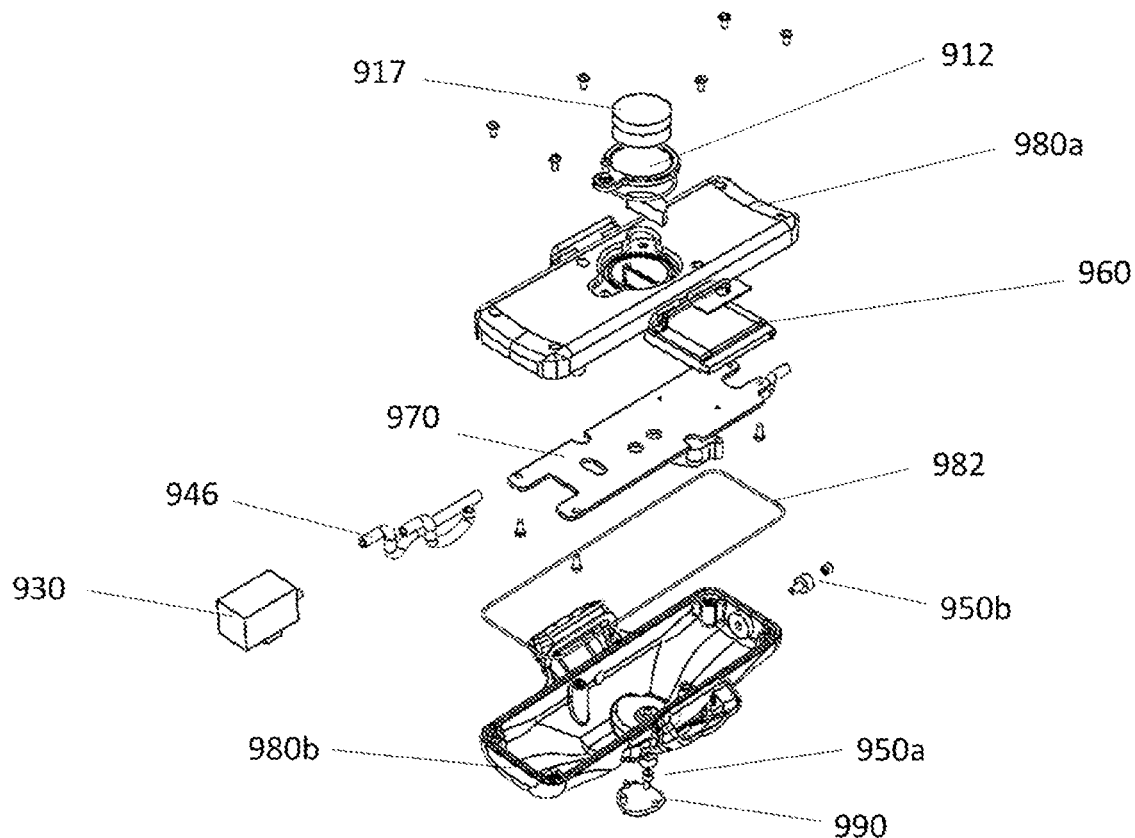
Figure 10:
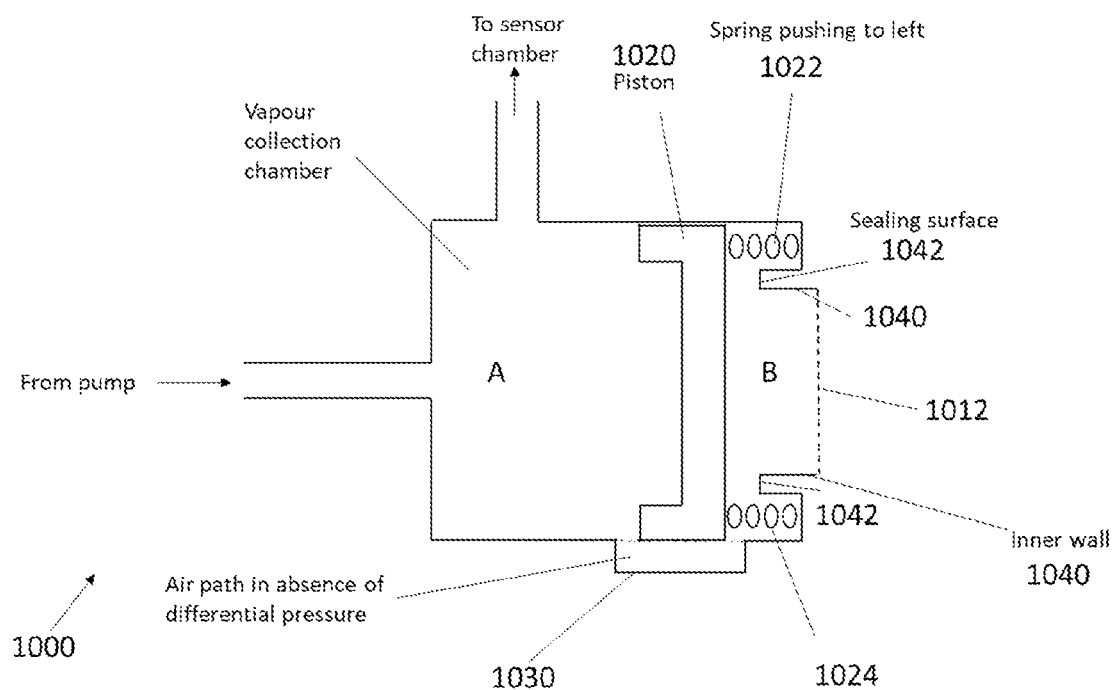
Figures 11A, 11B:
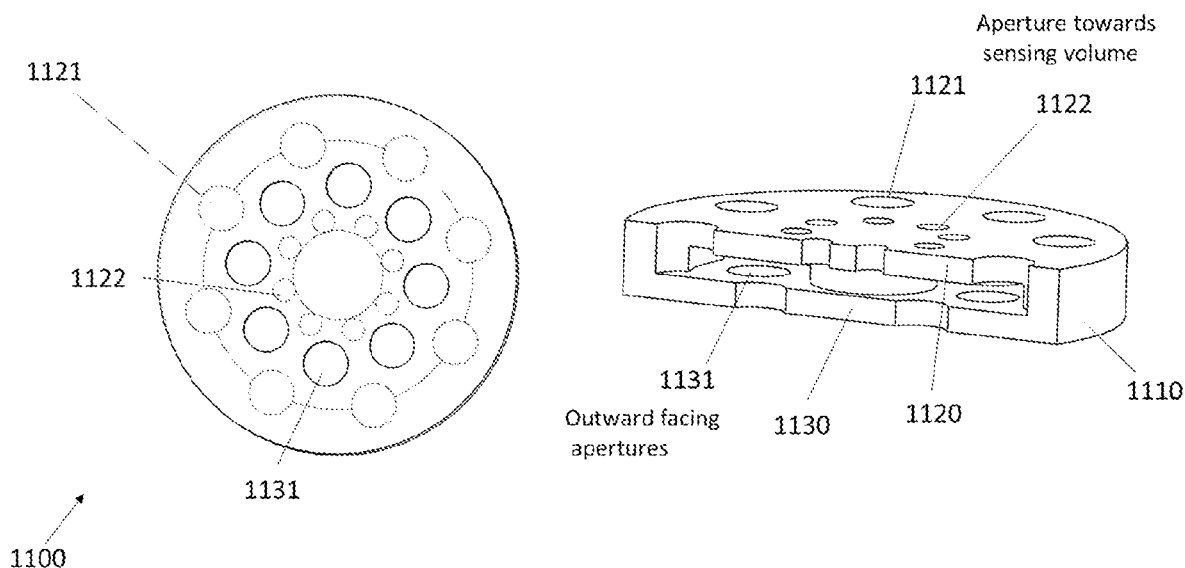
Figure 12:
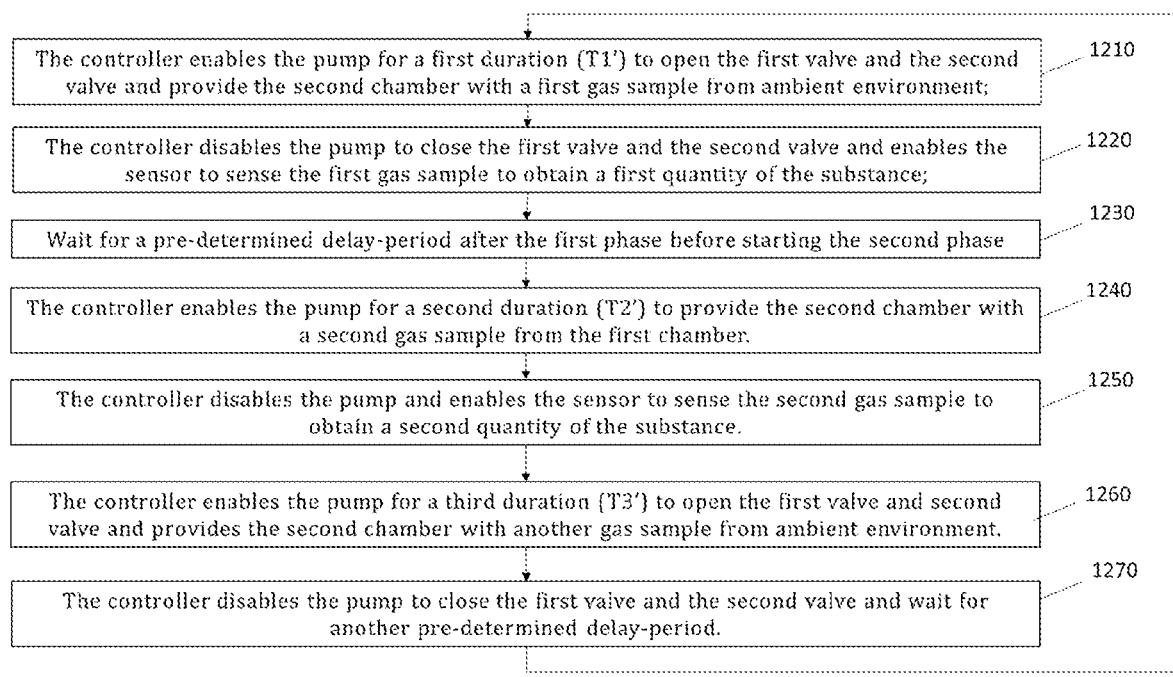

The disclosure is described in further detail below by way of example and with reference to the accompanying drawings, in which:

FIG. 1 is a is a flow chart of a method for detecting a substance of interest ingested by a subject, FIG. 2(a) is a profile view of a wearable device for implementing the method of FIG. 1, FIG. 2(b) is another profile view of the wearable device of FIG. 2(a), FIG. 3 is a diagram of a sensing arrangement for use in the wearable device of FIG. 2, FIG. 4 is a flow diagram of a measurement cycle for detecting a substance of interest ingested by a subject, FIG. 5 is a diagram of another sensing arrangement for use in the wearable device of FIG. 2, FIG. 6 is a diagram of a collection chamber provided with a piston mechanism, FIG. 7 is a diagram of a collection chamber provided with a mesh structure, FIG. 8 is a diagram of a collection chamber provided with a labyrinth structure, FIG. 9A is a top exploded view of a wearable tag, FIG. 9B is a bottom exploded view of the wearable tag of FIG. 9A, FIG. 10 is a diagram of a collection chamber provided with a piston mechanism, FIG. 11(a) is a top view of a port terminator, FIG. 11(b) is a cross section perspective view of the port terminator of FIG. 11(a), FIG. 12 is another flow diagram of a measurement cycle for detecting a substance of interest ingested by a subject.

FIG. 1 is a flow chart 100 of a method for sensing a substance of interest ingested by a subject. The substance of interest may be an intoxicating substance such as ethanol also referred simply as alcohol, or a pharmaceutical drug. The substance of interest may also be a metabolite obtained as a result of the subject ingesting ethanol or a pharmaceutical drug or another product.

At step 110 a sensing arrangement extending between a first port and a second port is provided. The sensing arrangement includes a first chamber adapted to collect gas from a skin region of the subject, a second chamber comprising a sensor adapted to sense the substance of interest, a pump, and a controller to control the pump and the sensor. A first flow-control device is provided at the first port and a second flow-control device is provided at the second port, respectively.

Each one of the first flow-control device and the second flow-control device is operable between a first state and a second state based on a pressure difference between an inner side and an outer side of the flow-control device. In the first state the flow-control device pass a gas flow and in the second state the flow-control device blocks the gas flow.

The first and second flow-control devices may be implemented in various ways. For instance, a flow-control device may be a valve such as pressure activated valve. Alternatively, a flow-control device may be a membrane, for instance waterproof and vapour permeable membrane allowing diffusion through it above a pre-determined pressure difference.

At step 120 the controller is operated in a first phase to sense a first gas sample from ambient environment, and in a second phase to sense a second gas sample from a skin region of the subject.

Using this approach, one can differentiate between a substance of interest emanating from the skin of the subject and either the same substance or a similar substance being present in the environment.

Upon identification of the substance of interest from a skin region of the subject indicating ingestion of the substance by the subject, various other actions may take place. For example, a time of detection and a location of the wearable device may be captured and stored. Optionally the time and location data may be transmitted to a remote device or server. Alternatively, or in combination an alarm signal may be generated and sent indicating that an intoxication event has occurred.

FIG. 2 illustrates a wearable device 200 for implementing the method of FIG. 1. In this example the wearable device 200 is a tag attachable on a limb of a subject such as the ankle or wrist. FIG. 2A shows the underside of the device to be applied onto a skin portion of the subject, while FIG. 2B shows the front of the device.

The device 200 includes a housing 210 also referred to electronic enclosure coupled to a strap 220 for attaching the device to a limb of the subject. The housing 210 has an inner portion to be applied to a skin region of the subject and an outer portion facing outwardly. The inner portion is provided with a diffusion membrane 230 for sampling air in proximity to the skin of the subject. The diffusion membrane 230 is preferably a waterproof membrane for instance an expanded PTFE membrane. The outer portion is provided with a first port 205a, also referred to as intake port, and a second port 205b, also referred to as outlet port.

A sensing arrangement not shown is provided within the housing 210 and extending between the first port 205a and the second port 205b. The sensing arrangement is adapted to sense a first gas sample to obtain a first quantity of a substance of interest and a second gas sample to obtain a second quantity of the substance. For example, the first quantity may be a first concentration and the second quantity a second concentration of the substance.

The wearable device 200 may be provided with a communication module for transmitting sensing data obtained by the sensing arrangement to a remote device 290 for data analysis. The communication module may be implemented in various fashions. For instance, the communication module may be adapted to send and/or receive data via a communication network such as a phone network or a computer network. The phone network may be a mobile network or a landline network. The communication module may include a transmitter such as a radio frequency RF transmitter to relay data over a telephone line or directly to the mobile phone network. The transmitter may also be implemented to communicate with a wireless local area network (LAN) such as a Wi-Fi LAN. The communication module may also include a receiver for receiving data from the remote device 290. The receiver and transmitter may be two separate devices or implemented as a transceiver. The remote device 290 may be a server provided with a processor adapted to calculate a difference between the first quantity and the second quantity and to return an output indicative of one of an ingestion and a lack of ingestion of the substance by the subject, based on the difference.

In another embodiment, the wearable device 200 may include an internal calculator or processor coupled to the sensing arrangement. In this case the calculator or processor may be configured to perform data analysis and optionally to send an output signal via the communication module. The output signal may be indicative of an ingestion or a lack of ingestion of the substance by the subject. For instance, the output signal may be a binary signal in which a positive signal, for instance a text message (Yes) or a visual indicator (Red) reveals the presence of the substance in the subject body and a negative signal, for instance No or Green, indicates that the substance is not present in the subject body. When the substance of interest has been identified as emanating from a skin region of the subject, a timer and a location device may be activated to record and store a time of detection and a position of the wearable device at the time of detection. Optionally, the time and location data may be transmitted to a remote device or server. Alternatively or in combination an alarm signal may be generated and sent indicating that an intoxication event has occurred.

The housing may also contain a device for detecting the position of the wearable device 200. For instance, the housing may be provided with a global navigation satellite system (GNSS) such as a global positioning system (GPS). The strap 220 may be provided with a tamper detection system adapted to detect removal or interference with the wearable device 200.

The wearable device 200 may also include a submersion detection system for identifying when the device is plunged under water or poured with water. The wearable device 200 is also provided with a power management system which may include a battery and a battery charging system.

It will be appreciated that in other embodiments the wearable device may be designed for use on a specific region of the subject body, which may or may not be a limb. In this case the housing and attachment mechanism may be adapted to fit a particular shape of the chosen body region.

FIG. 3 is a diagram of a sensing arrangement 300 that may be provided in the wearable device of FIG. 2. The sensing arrangement 300 extends between a first port 305a and a second port 305b and includes two chambers 310, 320 and a pump 330. In this embodiment the pump 330 is provided between a first chamber 310, also referred to as vapour collection chamber and the second chamber 320, also referred to as sensing chamber. Channel portions or ducts 342, 344, 346 and 348 are provides to allow a flux of gas to move between the various components of the sensing arrangement. The channels may be formed in different ways. For instance, a channel portion may be formed within a sealing block provided to seal two parts of the system together.

The first chamber 310 is adapted to collect gas from a skin region of the subject. The chamber 310 has an input coupled to the input port 305a via channel 342, an output coupled to the pump 330 via channel 344 and an opening covered with a diffusion membrane 312. A sensor 322 is located within the second chamber 322 for sensing the substance of interest potentially present in the volume of air of the second chamber 320. For example, the sensor 322 may be an electrochemical sensor. The second chamber 320 has an input coupled to the output of the pump 330 via channel 346 and an output coupled to the second port 305b via channel 348. The first port 305a is provided with a first valve 350a (intake valve), and the second port 305b is provided with a second valve 350b (outlet valve). The first and second valves are used to prevent ingress of water in the sensing arrangement, hence providing a waterproof system. The first and second valves are one-way valves allowing a fluid (liquid or gas) to flow through it in only one direction.

A controller 360 is provided to control the pump 330 and the sensor 322. The controller 360 is operable in a first phase to sense a first gas sample from ambient environment, and a second phase to sense a second gas sample from a skin region of the subject.

The first chamber 310 is located in a region of the housing such that in use, the diffusion membrane 312 is close or in contact with a skin portion of the subject. The input port 305a is located to receive ambient air from the subject environment. For instance, the input port 305a and the output port 305b may be pointing away from the membrane 312 and therefore in use away from the subject. The input port is preferably provided on the outer surface of the housing to access air with a minimum amount of transdermal substance (such as transdermal alcohol) from the subject. The output port can be positioned in various locations but preferably not in the region of the housing contacting the skin.

The valves can use one of many actuation methods. In the present example the first and second valves are implemented as pressure activated valves. Pressure activated valves are passive valves that open when a pressure difference in a preferred direction is imposed across them. They contain a natural hysteresis, so that the opening pressure is higher than the closing pressure. These valves are commercially available and designed to open at a relatively exact pressure.

The first valve 350a is a one way valve adapted to pass a gas flow when a pressure difference between the outer side and the inner side of the valve is above a first threshold value. The first valve 350a provided at the intake port may be chosen with an opening pressure difference ($P_{OUT}-P_{IN}$) determined by the external pressure the device needs to withstand. The first valve 350a is designed to remain closed until a given positive pressure is applied from the outside. Depending on the degree of waterproofing required, the first valve would open when a pressure gradient greater than that it would experience on submersion in the specified depth of water is applied. For instance, a tag specified to operate up to 10 meters under water would have an intake valve that opens at a pressure difference ($P_{OUT}-P_{IN}$) greater than 100 kPa, which would be generated by the pump pulling a partial vacuum inside the device. Thus the device would remain water-tight on submersion and air can be drawn into the system by the pump.

The second valve 350b is a one way valve adapted to pass a gas flow when a pressure difference between the inner side and the outer side ($P_{IN}-P_{OUT}$) is above a second threshold value. The second valve 350b provided at the output port may be chosen such that the valve opens with a relatively low pressure difference. The second valve 350b is designed to withstand a high positive pressure from the outside and to open at a pressure difference ($P_{OUT}-P_{IN}$) less than a negative threshold value for instance less than −100 Pa for example −5 kPa. Stated another way the second valve opens at a pressure difference $P_{IN}-P_{OUT}$ greater than a positive threshold value for instance greater than 100 Pa for example 5 kPa. The second valve is therefore designed with a small opening pressure allowing it to open when air is pushed out of the system. Thus even with a 10 m submersion specification the pressure difference ($P_{IN}-P_{OUT}$) to open the valve could be as low as 100 Pa. The second valve would not be forced open by the external water pressure as it opens with positive pressure from the inside of the tag and is designed to resist high pressure in the opposite direction.

If the pump 330 holds a pressure difference when stopped then it will prevent air flowing back out of the sensor chamber 320 into the vapour collection chamber 310. However, if this is not the case an isolation valve 352 can be inserted in the system between the vapour collection chamber 310 and the pump 330. The isolation valve may be designed to open using a relatively low pressure difference, for instance a pressure difference ($P_{IN}-P_{OUT}$) greater than 500 Pa such as for instance 1 kPa. In this way the isolation valve 352 can be open easily by the pump without interfering with the operation of the intake valve 350a.

Other optional components may be provided. For instance, the first chamber 310 may be provided with a temperature and humidity sensor 314. The temperature and humidity sensor 314 may be used to calculate a pressure of water in the first chamber 310.

The geometry of the first and second chambers 310 and 320, channels and input/output port may vary.

The first chamber 310 may have an internal volume V310 that is greater than the internal volume of the chamber 320. For instance V310=k V320, with k a multiplication factor that is function of the opening size of the valve 350a. The controller 360 may be configured to send a control signal for taking a measurement signal. For instance, the controller may be configured to verify that a particular condition is met before sending the control signal. For instance, the controller may receive a signal from a sensor indicating whether the device is underwater or not. Measurement is then initiated only if the device is not immersed under water. Other conditions may also be identified including a temperature of the gas sample, a pressure level or a degree of humidity within the first chamber 310 or other condition which may affect the accuracy of the measurement.

The sensor 322 may be coupled to a communication module or transmitter 370 for sending sensing data to a remote device for analysis. Optionally, a comparator circuit may be provided to compare different measurements of the sensor 322. In this case the communication module 360 may be arranged to send data from both the sensor 322 and the comparator circuit.

In some implementations a storage medium may be provided. The storage medium may be coupled to the sensor 322 and optionally to the communication module 370. The storage medium may be used to store sensing data from the sensor 322. The storage medium may also be configured to store calibration data to calibrate the sensor prior to measurement. For instance, the calibration data may include temperature and humidity calibration. The calibration data may be stored on the remote device/server and sent to the wearable device. For instance, the server may send a calibration update to a register file stored on the wearable device.

Since the system only uses a single sensor there is no need for cross calibration between multiple sensors.

The temperature and humidity sensors 314 may be implemented as two separate sensors or a as a combined sensor. A combined temperature and relative humidity sensor may be designed to calculate or measure a temperature of condensation, also referred to as dew point. This may be achieved by combining relative humidity and temperature measurements. As a result condensation within the chamber may be prevented.

In this example, the controller 360 may be configured to control the sensor 322 and the temperature and humidity sensor 314.

The internal walls of the first and second chambers 310, 320 and optionally of the channels 342, 344, 346, 348 may be coated. For instance, the internal walls may be coated with a hydrophobic coating, or a combination of hydrophobic and hydrophilic coatings arranged to direct water towards the output port.

Temperature and humidity may be measured at different points in time by the temperature and humidity sensor 314. For instance temperature and humidity may be monitored during the measurement cycle for example between the first phase and the second phase.

If further control of humidity is required, a water absorber, such as a silica-gel may be provided in the chambers. For instance, a screwing capsule containing silica-gel may be inserted into a region of the chamber or a separate region coupled to the chamber. Such capsules may be easily replaced at regular intervals along with a dry nitrogen purge as required.

In an alternative embodiment the first and second valves 350a and 350b are replaced by a first and a second membrane. The first membrane is adapted to allow diffusion through it when a first pressure difference is applied across the first membrane. Similarly the second membrane is adapted to allow diffusion through it when a second pressure difference is applied across the second membrane. As a result the various air components diffuse through the membrane when a certain pressure is applied across the membrane.

The first and second membranes may be waterproof membranes such as Polytetrafluoroethylene (PTFE) membranes. The PTFE membranes may be expanded PTFE membranes. PTFE membranes admit air under a differential pressure and act as diffusion membranes. Stated another way the flow over the membrane can be dictated by partial pressure as well as absolute pressure difference. The flow rate through the membrane is area-dependent and may be relatively large for example 100s of cc/min at dP~10 kPa, which is compatible with small pump characteristics.

Membranes may be selected to achieve a desired flow rate of diffusion. For instance, an expanded PTFE membrane can be chosen with a specific thickness and a specific density of pores. To achieve a relatively slow diffusion rate a tick membrane may be selected with relatively few pores. For a relatively fast diffusion rate a thin membrane can be chosen with a high density of pores. The diffusion membrane 312 may be chosen with a relatively slow diffusion rate compared with the first and second membranes provided at the input and output ports, respectively.

In operation the wearable device is attached onto a limb of the subject, for instance on the ankle such that the diffusion membrane 312 is facing a skin portion of the subject. The sensing system is then operated to perform successive measurement cycles.

FIG. 4 is a flow diagram illustrating a measurement cycle. The controller controls the pump 330 and the sensor 322 to performs successive measurement cycles. Each cycle includes a first phase (steps 410 and 420) for detecting the eventual presence of the substance of interest in the environment and a second phase (steps 440 and 450) for detecting the eventual presence of the substance of interest from the subject himself. At step 410, the controller enables the pump 330 for a first duration (T1) to open the first valve 350a and the second valve 350b and provide the second chamber with a first gas sample from ambient environment. The duration T1 should be long enough to reduce the internal pressure $P_{IN}$ below a pre-determined level so that the pressure difference ($P_{OUT}-P_{IN}$) across the first valve is sufficient to open the first valve. The step 410 is used to flush the system with ambient air to purge the whole volume of collected vapour. The pump pulls air from the vapour collection chamber 310 and provides it to the sensor chamber 320, and consequently pulls air from the distal side of the device into the vapour collection chamber and expels air from the sensor chamber via its exhaust port. At step 420 the controller disables the pump 330 to close the two valves 350a, 350b and enables the sensor 322 to sense the first gas sample to obtain a first quantity of the substance. For instance if the substance of interest is alcohol, the sensor 322 measures an alcohol concentration from ambient air.

At step 430 the controller waits for a pre-determined delay-period after the first phase before starting the second phase. This delay-period permits vapour emanating from the skin of the subject to diffuse through the membrane 312 into the collection chamber 310. For instance, the delay-period may last for several minutes, for instance between 10 and 15 minutes.

At step 440 the controller enables the pump for a second duration (T2) to provide the second chamber with a second gas sample from the first chamber. In the embodiment of FIG. 3 the pump 330 is activated so that the first valve remains closed and gas from the first chamber 310 is pumped into the second chamber 320. The second valves 305b opens to release the previous volume (first gas sample) and closes when the pump is deactivated.

The duration T2 should be sufficiently short so that the pressure difference ($P_{OUT}-P_{IN}$) across the first valve is not sufficient to open it (This is difference in the embodiment of FIG. 5 discussed below in which the first valve would open). Typically, a small quantity of air can be pumped into the sensing chamber, for instance enough to fill the sensor chamber with at least one or preferably two or three times its volume. At step 450 the controller disables the pump and enables the sensor to sense the second gas sample to obtain a second quantity of the substance. For instance, if the substance of interest is alcohol, the sensor 322 measures an alcohol concentration from the gas collected in the first chamber and emanating from the skin of the subject. Then the measurement cycle can be repeated.

Additional steps may be included for instance calculating a difference in concentration between the first measurement and the second measurement. The sensor 322 takes periodic measurements of substance concentration present in the chamber 320. The sensor outputs are then compared, for instance electronically. The sensor outputs may be digitised prior to comparison, thus allowing scaling to account for calibration factors and correction for example temperature variation. After calibration factors are accounted for the signals can be directly compared. The simplest comparison is a difference measurement:

$$\Delta S = S_2 - S_1$$

In which $S_1$ is the measurement signal from the volume of gas present in the chamber 320 at step 420 (first quantity of the substance corresponding to a baseline measurement) and $S_2$ is the measurement signal from the volume of gas of the second chamber 320 at step 450 (second quantity of the substance corresponding to substance emanating from the skin region of the subject). Therefore, a positive $\Delta S$ indicates that the substance is detected and emanates from the subject, while a negative or zero $\Delta S$ indicates that the substance is likely to be environmental in origin. A substance may be considered present in the subject body if $\Delta S$ is greater than a minimum positive threshold value.

The proposed waterproofing valve system allows substance (for instance alcohol) measurement without mixing air from the intake with that in the vapour collection chamber. As the intake valve 350a is shut until a significant vacuum is pulled by the pump, a portion of the air in the vapour collection chamber is pumped into the sensor chamber before the valve opens. In order for the sensor chamber 320 to be filled with a fresh sample, the volume of air pumped from the vapour collection chamber 310 should be greater than that of the sensor chamber 320 plus the pipework 346 intervening between the pump 330 and the sensor chamber 320 it by a factor N (for instance N=1, 2 or 3), at atmospheric pressure plus the outlet valve release pressure. This volume can be calculate using Boyles law. The volume of the vapour collection chamber can be calculated such that the sample volume has passed through the pump before the intake valve opens and the pump can be stopped such that no fresh air from the intake mixes with the sample volume prior to measurement by the sensor. After the measurement period the system is flushed with fresh air via the intake valve.

When the collection chamber 310 is provided with a temperature and humidity sensor 314, a humidity level can be calculated. For instance, a humidity level can be calculated after the collection chamber has been flushed with atmospheric air.

The humidity level increases as vapour diffuses through the membrane 312 into the vapour collection chamber 310.

FIG. 5 is a diagram of another sensing arrangement 500 that may be provided in the wearable device of FIG. 2.

The sensing arrangement 500 is similar to the sensing arrangement 300 of FIG. 3. The same reference numerals have been used to represent corresponding components and their description will not be repeated for sake of brevity. Like in the diagram of FIG. 3 the first and second valves 350a and 350b may be replaced by a first and a second membrane.

In this example the pump 330 is provided before the vapour collection chamber 310. Compared with the embodiment of FIG. 3, a smaller volume of air needs to be pumped to open the intake valve 350a. No vacuum is created in the collection chamber 310 and a lower differential pressure dP is applied through the membrane 312. The pressure in the vapour collection chamber is dictated by the outlet valve's characteristics rather than those of the intake valve.

However, when implementing the measurement cycle described in FIG. 4 (step 440), air can be mixed in the vapour collection chamber, hence reducing the concentration of the substance of interest to be detected.

Turbulences can cause mixing over large distances; however various mechanisms can be employed to reduce mixing mechanisms. For instance, a flow profile adjuster 510 can be provided to adjust the flow or gas entering the first chamber 310. The flow profile adjuster may be implemented in different ways. For instance, the flow profile adjuster may include a piston mechanism, a mesh structure, or a labyrinth structure.

FIG. 6 shows a collection chamber provided with a piston mechanism. The collection chamber 600 includes a piston 610, a pressure release valve 612 and a set of springs 614, 616. The piston 610 separates the chamber into two volume portions: A and B. The spring-loaded piston 610, 614, 616 and the pressure release valve 612 are configured such that the required sample volume is pushed into the sensor chamber without opening the pressure release valve 612. The pressure release value may be calculated based on spring compression and the piston travel required to shift a volume to the sensor chamber. However the pressure release valve would be designed to open during a flush step (410) of the measurement cycle. The pressure release valve should be made with a degree of hysteresis such that the piston can retract after the flush step.

FIG. 7 shows a collection chamber provided with a mesh structure. The collection chamber 700 includes a mesh structure 710, also referred to as flow-baffling mesh located at the input of the chamber. Optionally the mesh structure 710 may be provided with a pressure release valve 712 to facilitate the flush step of the measurement cycle. The chamber may be shaped to form an input portion designed to receive the mesh structure and an output portion to receive gas. The mesh structure may be designed with an inner volume that is sufficient to overfill the sensor chamber. In operation the mesh structure 710 forms no barrier to the diffusion of vapour; however it prevents a rapid flow of air from the intake to the rest of the chamber during movement of the skin-vapour sample (second gas sample) into the sensor chamber. In addition the mesh structure 710 permits a near unimpeded diffusion of all vapour from the vapour collection chamber. The mesh provides mechanical resistance to push against in such a way that air diffuses very slowly. In this way the concentration of the substance in the chamber remains relatively homogeneous. For instance, the substance concentration in the sample chamber 320 may be 90% of the substance concentration present in the collection chamber 310.

FIG. 8 shows a collection chamber provided with a labyrinth structure. The collection chamber 800 includes a labyrinth structure 810, also referred to as flow baffling labyrinth located at the input of the chamber. The labyrinth structure 810 is designed such that a turbid flow from the vapour collection chamber inlet is converted into a laminar flow. This allows a skin-vapour sample (second gas sample) to be pushed into the sensor chamber with minimal dilution.

The labyrinth structure can be designed in various ways. In the present example the labyrinth structure 810 is formed of an array of capillaries $811(i)$-$811(n)$. The labyrinth structure 810 splits the volume of the chamber between an input volume A located at the input side of the chamber and an output volume B. Alternatively, the labyrinth structure may include a plurality of disks, each disk having a set of apertures referred to as a hole pattern. The disks are arranged such that the holes patterns of the disks are offset with respect to each other such that the apertures are not aligned. As with the mesh structure, the labyrinth may form an internal volume equivalent to overfill the sensor chamber by a required factor. Preferably, the labyrinth structure should not overly impede diffusion of vapour into its volume. The labyrinth structure may also be replaced by a structure allowing to keep the flow laminar such as a curved funnel. In this case the curved funnel may be used in combination with a wall that divides the chamber in two portions.

FIG. 9A is a top exploded view of a wearable tag. FIG. 9B is a bottom exploded view of the wearable tag of FIG. 9A. The housing 980 is made in two parts: a bottom or proximal part 980*a* and a top or distal part 980*b* sealed together with an O-ring or gasket 982 which can be either made in mould or separately. The housing has two strap interface portions 984 to attach the strap to the housing. The diffusion membrane 912 is mounted in an interface plate which is in turn sealed to the bottom portion of the housing 980*a* by either an O-ring 913, a rubber gasket or a gasket created as part of the interface by a two-shot moulding process. The intake valve 950*a* is mounted on the intake port 905*a* in the top (distal) portion of the housing 980*b* to maximise the difference between the ambient and body-side collected substance concentrations (for instance alcohol concentrations). Similarly, the outlet valve 950*b* is mounted on the outlet port 905*b*. Both valves 950*a* and 950*b* can be sealed to the housing 980 by the mounting process. As explained above the outlet valve 950*b* could be mounted in other locations on the housing. A cap 990 is provided to prevent interference with the intake valve. In the embodiment this feature is a separate part which is fitted to the housing to cover the valve 950*a*. In a separate embodiment in which the inlet and outlet valves are located adjacently, the cap contains a wall feature that intervenes between the two valves to ensure that air exiting the outlet does not directly enter the intake. Between the bottom and the top part of the housing are provides the collection chamber 910, the pump 930 and the sensor chamber 920 connected between each other by tubing 946. A controller 970 and a battery 960 are provided to control and the device. A set of peelable layers 917 also referred to as cleaning layers are provided over the diffusion membrane 912 to extend its operating life. The peelable layers may include a sticky surface. The peelable/cleaning layers 917 could be made of a porous material or be provided with several holes and would have an interface layer (porous and spongy) between it and the diffusion membrane. The member 917 when made of a porous material may be made permanent and replaced with the rest of the mounting plate holding 912. The member 917 may be made of PTFE. The interface layer may aid adhesion to the skin.

FIG. 10 is a diagram of a collection chamber provided with a piston mechanism. The collection chamber 1000 has a diffusion membrane 1012. A piston 1020 is place within the chamber and facing the diffusion membrane 1012. The piston 1020 divides the chamber into two sub-chambers A and B. The piston 1020 is coupled to the walls of the chamber via a set of springs 1022, 1024. A recess 1030 is formed on a wall of the chamber to provide an air path between the sub-chamber A and the sub-chamber B. The walls of the chamber are shaped to form an inner wall 1040 and a sealing surface 1042 around the membrane 1012.

In operation the piston 1020 is used to prevent air exiting the chamber via the membrane when the pump is actuated. When the pump is not actuated the piston is in a natural position in which the air path between A and B is open. When the pump is actuated the pressure within the chamber increases and the piston is pushed towards the membrane hence closing the air path. The piston 1020 pushes against the sealing surface 1042 and forms a seal that stops air exiting the chamber via membrane 1012. The spring/piston mechanism can be made as an integral part, for instance as a curved thin piece of plastic that deforms to bind to the sealing surface and has 2 air paths when under no differential pressure.

A similar arrangement can be implemented when the pump is activated in reverse hence sucking air from the chamber (vacuum operation). In this case the sealing surface and the set of springs would be mounted on the other side of the piston.

FIG. 11 shows a port terminator designed to frustrate someone trying to insert an object in the sampled volume. The port terminator 1100 may be used with an input port or an output port. FIG. 11(*a*) is a top view of the port terminator. FIG. 11(*b*) is a cross section perspective view of the port terminator of FIG. 11(*a*).

The port terminator 1100 also referred to as port labyrinth is provided by a circular body 1110 having an inner portion 1120 forming a first plate, and an outer portion 1130 forming a second plate. The inner and outer portions are separated by a gap and opposite to each other. The inner portion 1120 has a first series of apertures 1121 distributed in a circular fashion across the surface, and a second series of apertures 1122 also distributed in a circular fashion. In this example the apertures 1121 have a diameter larger than the diameter of apertures 1122. The outer portion has a third series of apertures 1131 distributed in a circular fashion across the surface. The first, second and third series of apertures are arranged such that they do not overlap. In this example the series of apertures are distributed along three circular concentric paths, each path having a different radius. The three set of apertures form a labyrinth structure. If the input port is blocked, for instance by applying a piece of sticky-tape, then the total cavity aperture area of the wearable device is reduced. As a result the acoustic and or fluid-dynamic characteristics of the wearable device are also changed. Potential blockages can be identified by measuring the cavity resonance or pressure decay characteristic of the wearable device. Blockage may also be identified by monitoring a characteristic of the pump, for instance an electrical value associated with the operation of the pump.

The wearable device of the disclosure as described with respect to FIGS. 2 to 11 permits to differentiate between a substance of interest being emitted by the skin of the subject and either that substance, or a similar one, being present in the environment (i.e. ambient air). In addition, the wearable device is waterproof, hence allowing the subject wearing the device to take a bath.

The sensing arrangements presented above with respect to FIGS. 2 to 11 may include a timer and a location device for detecting the position of the device. For instance, the location device may include a satellite navigation system such as a GPS, it may also include a Wi-Fi detection system. The position of the device may also be obtained by triangulation such as GSM triangulation. When the substance of interest has been identified as emanating from a skin region of the subject, the timer and the location device may be activated to record and store a time of detection and a position of the wearable device at the time of detection. Optionally, the time and location data may be transmitted to a remote device or server. Alternatively or in combination an alarm signal may be generated and sent indicating that an intoxication event has occurred.

The sensing arrangements presented above with respect to FIGS. 2 to 11 may be modified to detect a specific substance of interest. In particular, the substance sensor may be selected to measure a particular substance or family of substances.

When considering the detection of alcohol, a catalytic sensor may be used. The principle of operation of gas detection using oxidation of the analyte of interest at the anode of a fuel cell is well known. It is used for instance in hand-held breathalysers. In these devices an alcohol arrives at the catalytic anode (platinum for instance) of the fuel cell and is oxidised to molecular acetic acid. The hydrogen generated drifts to the cathode where it combines with oxygen to form water. The resulting current registered is taken as an indication of the presence of alcohol. Such catalytic systems may be implemented in different fashions. For instance, a proton exchange membrane such as sulfonated tetrafluoroethylene membrane may be used.

Various substances of interest may be detected using an aptamer based sensor. Enzyme based detectors temporarily bind to the target molecule and act to catalyse a redox reaction involving that molecule. Aptamers bond to the target molecule and remain bonded. Both molecule types can be incorporated in a matrix which in turn is connected to the electrodes of a sensor yielding an electrical current. Additionally both types of molecule can be connected to a fluorescing agent such as green fluorescent protein, thus allowing optical detection using optical illuminate/response techniques.

Both enzyme and aptamer based detection techniques rely on relatively fragile biochemical molecules. Thus, a cartridge system would be required which would be replaced on a weekly basis and possibly a system where each reading is taken with a fresh sensor. Both enzyme and aptamer based sensors may be used for the detection of large molecules including among others: opiates, amphetamines, and cocaine.

FIG. 12 is a flow diagram illustrating another measurement cycle. The measurement cycle is similar to the measurement cycle described in FIG. 4 with the following modifications.

Each cycle includes a first phase (steps 1210 and 1220) for detecting the eventual presence of the substance of interest in the environment, a second phase (steps 1240 and 1250) for detecting the eventual presence of the substance of interest from the subject himself; and a third phase (steps 1260 and 1270) for resetting the system prior to a new cycle.

The steps 1210, 1220, 1230 and 1250 correspond to the steps 410, 420, 430, 440, 450 previously described with respect to FIG. 4; however, in this case the step 1210 has a time T1' that may be shorter than the time T1 of step 410.

The duration T1' should be long enough to reduce the internal pressure $P_{IN}$ below a pre-determined level so that the pressure difference ($P_{OUT}-P_{IN}$) across the first valve is sufficient to open the first valve. The time T1' may be shorter than the predetermined delay period of step 1230.

The time T1' may be chosen to be equal or substantially equal to the time T2' of step 1240. This improves the accuracy with which the first quantity of the substance obtained at step 1220 and the second quantity of the substance obtained at step 1250 can be compared.

The two additional steps 1260 and 1270 are used to reset the system before repeating the measurement cycle.

At step 1260 the controller enables the pump for a third duration T3' to open the first valve and the second valve. This provides the second chamber with another gas sample from ambient environment. The third duration T3' may be chosen to be long enough to purge or flush the system of all vapour admitted during the preceding steps. For instance, the time T3' may be chosen to be greater than T1' or T2'. The times T1', T2' and T3' may have the following relationship: T1'=T2' and T3'>T1'.

At step 1270 the controller disables the pump to close the first valve and the second valve. The controller then waits for another pre-determined delay-period. This pre-determined delay-period may be chosen to be long enough to permit the sensor to settle before taking a measurement. The sensor settling time may vary from sensor to sensor and may be in the order of a few tens of seconds.

It will also be appreciated that the measurement cycle as described in FIG. 4 or FIG. 12 may be modified in various ways. For instance, the sensor may be enabled at different points in the measurement cycle and left on for various steps or for all the steps of the measurement cycle. For example, in FIG. 12, the sensor could be enabled once after step 1260 and left enabled for multiple measurement cycles. In another example the sensor may be enabled between the first phase and the second phase.

A skilled person will therefore appreciate that variations of the disclosed arrangements are possible without departing from the disclosure. Accordingly, the above description of the specific embodiments is made by way of example only and not for the purposes of limitation. It will be clear to the skilled person that minor modifications may be made without significant changes to the operation described.

The invention claimed is:

1. A waterproof wearable device for sensing a substance ingested by a subject, the wearable device comprising:
   a sensing arrangement extending between a first port and a second port, the sensing arrangement comprising:
   a first chamber adapted to collect gas from a skin region of the subject;
   a second chamber comprising a sensor adapted to sense the substance;
   a pump;
   a first flow-control device provided at the first port;
   a second flow-control device provided at the second port;
   a controller adapted to control the pump and the sensor, the controller being operable in a first phase to sense a first gas sample from ambient environment, and a second phase to sense a second gas sample from a skin region of the subject;
   wherein in the first phase the controller is configured to enable the pump for a first duration to open the first flow-control device and the second flow-control device and provide the second chamber with a first gas sample from ambient environment;
   wherein in the second phase the controller is configured to enable the pump for a second duration to provide the second chamber with a second gas sample from the first chamber; and
   wherein each one of the first flow-control device and the second flow-control device is operable between a first state and a second state based on a pressure difference between an inner side and an outer side of the flow-control device, wherein in the first state the flow-control device passes a gas flow and wherein in the second state the flow-control device stops the gas flow.

2. The wearable device of claim 1,
   wherein in the first phase the controller is configured to disable the pump to close the first flow-control device and the second flow-control device; to enable the sensor to sense the first gas sample to obtain a first quantity of the substance; and wherein in the second phase the controller is configured to disable the pump; to enable the sensor to sense the second gas sample to obtain a second quantity of the substance.

3. The wearable device of claim 2, wherein the first duration is greater than the second duration or wherein the first duration is substantially equal to the second duration.

4. The wearable device of claim 1, wherein the controller is configured to delay a start of the second phase by a delay-period, and wherein during the delay-period gas is diffusing from the skin region into the first chamber.

5. The wearable device of claim 1, wherein the controller is operable in a third phase, wherein in the third phase the controller is configured to enable the pump for a third duration to open the first flow-control device and the second flow-control device and provide the second chamber with another gas sample from ambient environment.

6. The wearable device of claim 5, wherein in the third phase the controller is configured to disable the pump to close the first flow-control device and the second flow-control device; and to delay a start of the first phase by a predetermined delay-period.

7. The wearable device of claim 1, wherein the pump is provided between the first chamber and the second chamber.

8. The wearable device of claim 1, wherein the first chamber is provided between the pump and the second chamber.

9. The wearable device of claim 8, wherein the first chamber comprises a flow profile adjuster.

10. The wearable device of claim 9, wherein the flow profile adjuster is adapted to provide a laminar flow at an input of the first chamber, and wherein the flow profile adjuster comprises a mesh structure or a piston mechanism or a labyrinth structure.

11. The wearable device of claim 1, wherein the first chamber comprises a membrane applicable on the skin region of the subject.

12. The wearable device of claim 11, wherein the first chamber comprises a piston mechanism.

13. The wearable device of claim 12, comprising one or more removable layers provided on an outer surface of the membrane.

14. The wearable device of claim 1, wherein the first flow-control device is a first-valve and wherein the second flow-control device is a second-valve, and wherein the first flow-control device is a first-membrane and the wherein the second flow-control device is a second-membrane.

15. The wearable device of claim 1, wherein the second chamber comprises at least one of a temperature sensor and a humidity sensor.

16. The wearable device of claim 2, further comprising a calculator adapted to calculate a difference between the first quantity and the second quantity and to return an output indicative of one of an ingestion and a lack of ingestion of the substance by the subject, based on the difference.

17. The wearable device of claim 1, wherein the wearable device comprises a communication module adapted to send data from the sensing arrangement.

18. The wearable device of claim 1, wherein at least one of the first port and the second port are provided with a terminator.

19. The wearable device of claim 1, further comprising a timer and a location device for acquiring time and a location data, wherein upon identification of the substance, the wearable device is configured to perform at least one of storing and transmitting the time and location data, and wherein the wearable device comprises a submersion detector adapted to detect when the device is put underwater.

20. The wearable device of claim 1, wherein the wearable device is included within a system comprising:
a processor adapted to calculate a difference between a first quantity of the substance and a second quantity of the substance and to return an output indicative of one of an ingestion and a lack of ingestion of the substance by the subject, based on the difference.

21. A method of sensing a substance ingested by a subject, the method comprising:
providing a sensing arrangement extending between a first port and a second port, the sensing arrangement comprising a first chamber adapted to collect gas from a skin region of the subject; a second chamber comprising a sensor adapted to sense the substance; a pump; a first flow-control device provided at the first port and a second flow-control device provided at the second port, wherein each one of the first flow-control device and the second flow-control device is operable between a first state and a second state based on a pressure difference between an inner side and an outer side of the flow-control device, wherein in the first state the flow-control device passes a gas flow and wherein in the second state the flow-control device stops the gas flow,
providing a controller to control the pump and the sensor, and
operating the controller in a first phase to sense a first gas sample from ambient environment, and in a second phase to sense a second gas sample from a skin region of the subject;
wherein in the first phase the controller is configured to enable the pump for a first duration to open the first flow-control device and the second flow-control device and provide the second chamber with a first gas sample from ambient environment, wherein in the second phase the controller is configured to enable the pump for a second duration to provide the second chamber with a second gas sample from the first chamber.

22. The method of claim 21, further comprising:
obtaining a first quantity of the substance from the first gas sample and a second quantity of the substance from the second gas sample,
calculating a difference between the first quantity and the second quantity, identifying one of an ingestion and a lack of ingestion of the substance based on the difference.

* * * * *